United States Patent [19]
Held, III et al.

[11] Patent Number: 6,005,668
[45] Date of Patent: Dec. 21, 1999

[54] DETECTING DEFECTS IN PLASTIC AND SIMILAR SURFACES

[75] Inventors: Theodore D. Held, III, Grosse Pointe Farms; Gerald J. Cormier, Oxford, both of Mich.

[73] Assignee: Henkel Corporation, Gulph Mills, Pa.

[21] Appl. No.: 09/112,389

[22] Filed: Jul. 9, 1998

Related U.S. Application Data

[60] Provisional application No. 60/052,471, Jul. 14, 1997, and provisional application No. 60/057,528, Sep. 4, 1997.

[51] Int. Cl.[6] .................................................. G01N 21/55
[52] U.S. Cl. ................................................ 356/371; 436/5
[58] Field of Search ..................................... 356/371, 376, 356/239.8, 237.3; 436/5

[56] References Cited

U.S. PATENT DOCUMENTS

| | | | |
|---|---|---|---|
| 4,514,045 | 4/1985 | Huffman et al. | 356/351 |
| 4,629,319 | 12/1986 | Clarke et al. | 356/237 |
| 5,745,238 | 4/1998 | Long et al. | 356/376 |

*Primary Examiner*—Frank G. Font
*Assistant Examiner*—Tu Nguyen
*Attorney, Agent, or Firm*—Ernest G. Szoke; Wayne C. Jaeschke; Norvell E. Wisdom, Jr.

[57] ABSTRACT

A "highlighter" liquid for detecting cosmetic defects in non-metallic surfaces, particularly those intended for high quality automotive finishes comprises organic substances each molecule of which contains at least one continuosly chemically bonded chain or ring of atoms in which there are at least two carbon atoms and at least two oxygen, nitrogen, sulfur, and phosphorus heteroatoms, the carbon atoms and heteroatoms being arranged in such an order along the chain or ring that (i) each heteroatom is bonded to at least one carbon atom and (ii) the chain does not include more than three consecutive continuosly chemically bonded carbon atoms. Particularly suitable materials include glycerin, propylene glycol, low molecular weight glycol condensation polymers, and monoethers of these glycol condensation polymers. Water is also usually present in the highlighter liquid, which has a long open time and does not damage the substrate even if left in place for a day or more.

20 Claims, No Drawings

DETECTING DEFECTS IN PLASTIC AND SIMILAR SURFACES

CROSS-REFERENCE TO RELATED APPLICATIONS

Priority for this application is claimed under 35 U.S.C. § 119(e) from U.S. Provisional Application Ser. No. 60/052,471 filed Jul. 14, 1997, and 60/057,528, filed Sep. 4, 1997.

STATEMENT REGARDING FEDERALLY SPONSORED RESEARCH OR DEVELOPMENT

Not applicable.

BACKGROUND OF THE INVENTION

This invention relates to compositions and processes for detecting geometric irregularities in shaped non-metallic surfaces over at least part of which pure liquid water will not spontaneously spread. The invention more particularly relates to detecting such irregularities in surfaces of articles of manufacture made of plastics, including thermoplastics, more particularly articles constituted predominantly of "engineering" plastics used as parts of automobile bodies. (For convenience and brevity, the remainder of the description below will generally refer only to plastic surfaces. However, it should be understood that the invention may be applied, mutatis mutandis, to any other non-metallic surface over which pure water does not spontaneously spread. One common example of such a surface would be a conventionally primer coated metal surface, when the primer is not glossy, but a final surface finish over the primer will make the finished surface glossy. A surface formed by any other non-glossy and non-metallic intermediate coating, e.g., a primed surface of plastic sheet molding compound that is intended to have a final glossy surface, can also advantageously be treated according to the present invention.) Such articles are usually shaped by molding and usually emerge from molding with a surface smooth to the touch but often not smooth enough to be reflective or glossy. This type of surface finish with low specular gloss will usually be described hereinafter as "matte". Visual examination of a matte surfaced molded plastic part only rarely reveals any visually perceptible non-uniformities in the surface. Particularly difficult to detect are shallow but larger scale non-uniformities often described as "waviness" or some similar term.

If such a molded plastic surface is intended for use on the exterior of an automobile body, the surface is often coated with the same materials and processes as are used for the exterior finish for metallic parts of automobile bodies. After such coating has been completed, it has been fairly often observed that the coated plastic surface appears blemished by visually perceptible non-uniformity in one or more of gloss, color, or surface texture in some parts of, usually in small spots or streaks on, the coated surface, and that these defects can be determined to be due to corresponding irregularities in the underlying surface rather than to flaws in the coating itself. Such surface blemishes, often called in the art and referred to later herein as "cosmetic" blemishes, defects, flaws, or a like term, are generally unacceptable to buyers of new automobiles.

The cost of exterior automotive finishes, which often require at least three separate coating compositions and processes to complete, is quite high, and finished parts found to have a defective surface usually must be scrapped. If the defects can be discovered before finishing begins, at least the cost of the finishing of a defective part will be avoided, and sometimes the defective part can economically be reworked to a satisfactory surface quality and eventually used. As a result, methods, simpler and less costly than completion of the normal finishing process, of detecting surface defects on plastic articles of manufacture are highly desirable.

Accordingly, one object of this invention is to provide a process, and any composition(s) needed therein, for making readily visually detectable any surface irregularities in plastic surfaces, particularly those having a matte finish, that are not readily detectable while the surface remains unreflective but will become readily visually apparent when these plastic surfaces are given a coating with a conventional autobody exterior finish. In order to be practically useful, any such process according to the invention must be less costly than a process of forming a conventional exterior autobody finish on the plastic surface. Preferably, a process according to the invention also achieves at least one, and most preferably all, of the following objectives: Any material, other than a component of the desired final coating for the article as it is to be used by an ultimate consumer, that is coated onto the surface to be tested is easily removable from the surface, most preferably by a simple water rinse; no deterioration in physical strength of the article having the plastic surface being tested for irregularity results from the detection process; no reduction in adhesion of any desired final coating occurs as a result of the detection process; little or no corrosion of equipment used in the process occurs; and the period of time during which the detection may be completed, hereinafter usually denoted as the "open time", is at least, with increasing preference in the order given, 1.0, 2.0, 3.0, 4.0, 5.0, 7.0, 10, or 15 minutes (hereinafter usually abbreviated as "min"); or 1, 3, 6, 12, 24, 48 or 72 hours. The conditions most favoring visual perceptibility of cosmetic blemishes generally require the surface being evaluated to be vertical or nearly vertical, so that these preferred minimal limits on open time are to be understood as measured on a vertical surface; any other angle of orientation of the surface should normally result in a longer open time. Other concurrent and/or alternative objects will be apparent from the description below.

Except in the claims and the operating examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred, however. Also, throughout the description, unless expressly stated to the contrary: percent, "parts of", and ratio values are by weight or mass; the term "polymer" includes "oligomer", "copolymer", "terpolymer" and the like; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description or of generation in situ within the composition by chemical reaction(s) noted in the specification between one or more newly added constituents and one or more constituents already present in the composition when the other constituents are added, and does not necessarily preclude unspecified chemical interactions among the constituents of a mixture once mixed; specification of constituents in ionic form additionally implies the presence of sufficient counterions to produce electrical neutrality for the composition as a whole and for any substance added to the composition; any counterions thus implicitly specified preferably are selected from among other constituents explicitly specified in ionic form, to the extent possible; otherwise such counterions may be freely selected, except for avoiding counterons that act adversely to an object of the invention; the word "mole" means "gram mole", and the word itself and all of its grammatical variations may by used for any chemical species defined by all of the types and numbers of atoms present in it, irrespective of whether the species is ionic, neutral, unstable, hypothetical, or in fact a stable neutral substance with well defined molecules; and the terms "solution", "soluble", "homogeneous", and the like are to be understood as including not only true equilibrium solutions or homogeneity but also dispersions that show no visually detectable tendency toward phase separation over a period of observation of at least 100, or preferably at least 1000, hours during which the material is mechanically undisturbed and the temperature of the material is maintained within the range of 18–25° C.

BRIEF SUMMARY OF THE INVENTION

It has been found that at least the minimum object, and in preferred embodiments two or more objects, of the invention as stated above can be achieved by applying over a surface to be tested for susceptibility to cosmetic blemishing a suitably selected liquid composition that forms a glossy and specularly reflective liquid film over all of the surface to be tested, this film persisting in place over the surface for a sufficient time to enable an inspector to examine the exterior surface of the liquid film, under the same lighting conditions as are used to examine conventionally finished metal substrate exterior body parts for automobiles, for any inconsistencies in reflectivity that highlight surface irregularities in the solid surface most nearly underlying the part of the liquid coating exhibiting a reflectivity that is inconsistent with that of the bulk of the liquid coating. If no such inconsistencies are observed, the plastic surface so tested can be reliably expected to have a cosmetically flawless surface when properly finished with a conventional autobody exterior finish system.

BRIEF DESCRIPTION OF THE SEVERAL VIEWS OF THE DRAWING

Not applicable.

DETAILED DESCRIPTION OF THE INVENTION

An important part of preferred embodiments of this invention is the selection of a suitable liquid composition for forming and constituting the glossy and specularly reflective liquid film required by the invention. For economy and avoidance of flammability hazards, a water-based liquid is preferred. However, when many water-based liquids are applied as a coating on the plastic materials of greatest current commercial interest, a phenomenon, which has been named "Swiss-cheese-dewetting", has been observed: An initially formed film of these liquids is glossy and specularly reflective as required, but for liquids susceptible to Swiss-cheese-dewetting, as the water in the liquid film drains and evaporates, small "holes" in the film, the term "holes" being understood to include areas of visually obvious non-uniform thinning of the initially applied composition as well as complete disappearance or drying of this initially applied composition, rapidly develop spontaneously as water is lost from the initially applied composition. At this point the liquid surface coating looks geometrically like a thin slice of Swiss cheese, because it has apparently randomly placed mutually distinct holes of various sizes within a continuous connected sheet. These initially formed holes grow in size as the liquid around their perimeters moves predominantly away from rather than toward the initial perforation site. In severe cases, this phenomenon eventually results in the collection of all the remaining liquid from the initially applied composition into discrete drops on the surface. The development of one or more holes that individually or collectively impair the overall specular reflectivity of the liquid coating surface to an extent that is readily perceptible visually by an inspector marks the end of the open time for a film, because even one defect will cause the surface to be rated as unacceptable.

Preferred compositions for use according to the invention comprise, preferably consist essentially of, or more preferably consist of:

(A) a concentration of a dissolved component selected from a group consisting of organic substances each molecule of which contains at least one continuously chemically bonded chain or ring of atoms in which there are at least two, or preferably at least three, carbon atoms and at least two atoms selected from a group of heteroatoms, said group of heteroatoms consisting of oxygen, nitrogen, sulfur, and phosphorus, preferably oxygen and nitrogen, said carbon atoms and heteroatoms being arranged in such an order along said continuously chemically bonded chain or ring that (i) each heteroatom is bonded to at least one carbon atom and (ii) the chain does not include more than three consecutive continuously chemically bonded carbon atoms; this condition does not exclude bonding of either a carbon atom or a heteroatom within said continuously chemically bonded chain or ring to other carbon atoms not part of said continuously chemically bonded chain or ring, and the bonding required within said chain or ring may include double or triple as well as single bonds; and, optionally, one or more of the following components:

(B) a concentration of a component of one or more surfactants that consists of molecules that are not part of component (A);

(C) water;

(D) a component of pH adjusting agent that is not part of any of components (A), (B), and (C);

(E) a component of preservative material that is not part of any of components (A), (B), (C), and (D);

(F) a component of viscosity adjusting agent that is not part of any of components (A), (B), (C), (D), and (E); and (G) a component of humectant material that is not part of any one of components (A), (B), (C), (D), (E), and (F).

Component (A) as described above is normally the predominant constituent, with the possible exception of water, in a liquid composition used according to the invention to form a glossy and specularly reflective liquid film. The combination of hydrophilic and hydrophobic portions in molecules constituting component (A) is believed to make them particularly suitable for forming the bulk of the glossy and specularly reflective liquid film required in a process according to the invention. Additionally, molecules of this type with sufficiently high molecular weights to give them low volatility at normal ambient human comfort temperatures, i.e., 18–25° C., to favor long open times, are readily available commercially.

Because of their low cost and ready availability, particularly preferred groups of materials for component (A) are (i) those materials, denoted herein as "glycols" and "glycol polymers", the molecules of which conform to the chemical formula HO—$(C_nH_{(2n+1-m)}O_m)_p$—H, where n is an integer from 2 to 6, preferably from 2 to 4, more preferably 2 or 3, most preferably 2; m, for each molecule, is an integer with a value not greater than the value of n for the same molecule, preferably not greater than 2 and more preferably, unless p=1, exactly 1; and p, for each molecule, is an integer with a value of 1 for glycols and a value of at least 2 for glycol polymers (for glycol polymers, any one or more of n, m, and p may have an average non-integral value for component (A) as a whole); and (ii) the mono- and di-ethers of such glycols and glycol polymers, said ethers having terminal alkyl moieties with from 1 to 6, preferably from 1 to 4, more preferably from 1 to 3, carbon atoms. If p is two or more, the values of n and m may be the same or different from one to another of the p instances of the moiety —$C_nH_{(2n+1-m)}O_m$— in each molecule, and if n is greater than 2, all except two of the carbon atoms in each —$C_nH_{(2n+1-m)}O_m$— moiety may be out of the continuously chemically bonded chain that is necessarily present in a moiety —$C_nH_{(2n+1-m)}O_m$—$C_{n'}H_{(2n'+1-m')}O_{m'}$— which is present in each molecule of a glycol polymer. (If n is always four or greater, some of the carbon atoms present in each —$C_nH_{(2n+1-m)}O_m$— moiety must be out of the continuously chemically bonded chain in at least one —$C_nH_{(2n+1-m)}O_m$—$C_{n'}H_{(2n'+1-m')}O_{m'}$— moiety in each molecule, in order for the molecule to satisfy the conditions for belonging to component (A).) Polymers of ethylene and/or propylene glycol(s) in which there are at least two glycol units are, along with glycerin and propylene glycol itself, particularly preferred constituents for component (A).

In order to achieve an optimum balance between volatility and tendency of an initially formed glossy and specularly reflective liquid film to solidify and/or develop haziness during drying, the weight average molecular weight of any glycol polymers portion of component (A) in the film, which glycol polymers portion may or may not constitute all of component (A), preferably is at least, with increasing preference in the order given, 100, 150, 200, 250, 300, 325, 350, 375, or 395 and independently preferably is not more than, with increasing preference in the order given, 4000, 3000, 2000, 1750, 1500, 1250, 1000, 750, or 500. (Haziness in the film is disadvantageous because it may, and if severe enough will, make the desired defect detection impossible as long as it persists. In some instances, it has been observed that an initially transparent liquid coating becomes hazy during drying and then becomes transparent again after further drying. Compositions with this property are often acceptable for use according to the invention, but are generally not preferred, because any period of haziness subtracts from the effective open time available with the particular liquid composition. Substantial fractions of glycol polymers with molecular weights above 1000, which, especially if they are homopolymers of ethylene glycol, are likely to be solid rather than liquid at normal ambient temperature, have been observed to favor development of haziness for at least a brief interval during drying of the glossy and specularly reflective liquid films used as part of a process according to the invention.)

Another type of generally highly satisfactory and commercially available materials for component (A) as described above are ethers, particularly monoethers, of glycol polymers. Non-limiting examples of these materials include diethylene glycol monobutyl ether, tripropylene glycol monomethyl ether, and dipropylene glycol mono-n-propyl ether. For these materials, a somewhat lower average molecular weight than for the glycol polymers themselves is preferred. Specifically, the weight average molecular weight of any ethers of glycol polymers present in component (A) of a composition to be used according to the invention to form a glossy and specularly reflective liquid film preferably is at least, with increasing preference in the order given, 80, 100, 120, 140, 150, 160, 170, 180, or 185 and independently preferably is not greater than, with increasing preference in the order given, 500, 400, 350, 300, 280, 260, 250, 240, 230, or 225.

Among the monomeric glycols as defined above that may be constituents of component (A) according to the invention, glycerin is most preferred, propylene glycol is nearly as preferred as glycerin, and ethylene glycol is distinctly less preferred, although suitable.

A normally preferred at least partial constituent of component (A) as described above is material with stronger surfactant properties than most of the glycols, glycol polymers and their ethers. One especially preferred type of such materials is constituted of molecules that, in addition to having in each molecule at least one continuously chemically bonded chain or ring of atoms in which there are at least two carbon atoms and at least two heteroatoms, as required to be part of component (A), also have at least one hydrophobe moiety that satisfies all of the following conditions: (i) it has not more than two open valences; (ii) it has a number of carbon atoms that is at least, with increasing preference in the order given, 8, 10, 12, 14, or 16; (iii) it contains no atoms other than carbon, hydrogen, nitrogen, oxygen, phosphorus, sulfur, and halogens and preferably, primarily for reasons of economy, contains no halogen atoms or more preferably no halogen, phosphorus, or sulfur atoms; (iv) if it contains any atoms of nitrogen, oxygen, phosphorus, or sulfur, it contains such atoms in a number having a ratio to the number of carbon atoms in the same moiety that is not more than, with increasing preference in the order given, 0.34:1.0, 0.30:1.0, 0.25:1.0, 0.20:1.0, 0.15:1.0, 0.10:1.0, or 0.05:1.0. (It should be noted that block copolymers of propylene oxide and ethylene oxide, if the blocks of polypropylene oxide are long enough, can satisfy this definition if they have surfactant properties, i.e., if they cause a reduction in the surface tension of water when dissolved therein.)

A particular type of surfactant constituent of component (A) that is preferred in certain instances is one in each molecule of which there is a substituted imidazoline moiety (which itself satisfies the structural formula conditions for being a part of component (A)), with a hydrophobic moiety attached to the carbon atom in the imidazoline moiety that is directly bonded to both nitrogen atoms in the imidazoline moiety, and preferably also at least one, or more preferably two, substituent moieties bonded to nitrogen atom(s) in the imidazoline moiety, these substituent moieties being selected from the group consisting of (i) hydroxyalkyl moieties, preferably hydroxymethyl and hydroxyethyl moieties, more preferably the latter; (ii) carboxyalkyl moieties (i.e., moieties derived from carboxylic acids by removing from each molecule thereof one hydrogen atom that is not the one that is part of the characteristic —COOH moiety of a carboxylic acid), preferably those derived from propanoic or 2-methyl propanoic acid, more preferably the former; and (iii) carbonate moieties. 2-Alkylimidazoline moiety containing surfactants of this type often impart two useful properties to compositions for forming glossy and specularly reflective liquid film in a process according to the invention: good wetting of most engineering plastic surfaces and freedom from haziness at any stage of drying. However, these surfactants are considerably more expensive than most other suitable surfactants that can constitute part of component (A) as defined above, and therefore, at least for reasons of economy, preferably are used, if at all, only when and to the extent that these advantages are needed. The carboxyalkyl moiety may be free acid or a salt, preferably a salt with an alkali metal cation. One particularly preferred embodiment of this type of surfactant is one available commercially from Mona Industries as MONATERIC™ Cy Na 50 and reported by its supplier to be a 50% solution in water of the sodium salt of 3-[1-(2-hydroxyethyl)-2-capryl-3-imidazolinyl] propanoic acid. Another particularly preferred embodiment of this type of surfactant is one available commercially from Lonza, Inc. as AMPHOTERGE™ KJ-2 and reported by its supplier to be a 40% solution in water of substituted imidazoline dicarbonate molecules.

Component (A) in total preferably constitutes at least, with increasing preference in the order given, 5.0, 7.0, 8.0, 9.0, 10.0, or 11.0, and unless substantially all of component (A) has surfactant properties, still more preferably constitutes, with increasing preference in the order given, at least 12.0, 12.3, 12.6, 12.9, 13.2, 13.5, 13.7, or 13.9% of a total composition to be used for forming a glossy and specularly reflective liquid film in a process according to the invention. Independently, surfactants belonging to component (A) preferably constitute at least, with increasing preference in the order given, 0.15, 0.30, 0.50, 0.70, 0.80, 0.90, 1.0, or 1.1% of a total composition to be used for forming a glossy and specularly reflective liquid film in a process according to the invention, and, if the surfactant portion of component (A) does not include alkyl imidazoline moiety containing surfactants in an amount of at least, with increasing preference in the order given, 0.50, 0.60, 0.70, 0.80, 0.90, or 1.0% of the total composition, more preferably constitutes at least, with increasing preference in the order given, 2.0, 3.0, 3.5, 4.0, 4.5, 5.0, or 5.5% of the total composition. Also and independently, molecules selected from a group consisting of (i) homopolymers of ethylene glycol, (ii) monoethers of homopolymers of ethylene glycol, monoethers of homopolymers of propylene glycol, and monoethers of copolymers of both ethylene and propylene glycols, and (iii) glycerin and propylene glycol preferably constitute at least, with increasing preference in the order given, 3.0, 4.5, 6.0, 7.5, 9.0, 9.5, 10.0, 10.5, 11.0, 11.5, 12.0, or 12.5% of a total composition to be used for as forming a glossy and specularly reflective liquid film in a process according to the invention, and, unless at least, with increasing preference in the order given, 0.5, 1.0, 1.5, 2.0, 2.5, 3.0, 4.5, 6.0, 7.5, 9.0, 9.5, or 10.0% of the total composition consists of glycerin, propylene glycol, and mixtures thereof, molecules selected from a group consisting of (i) homopolymers of ethylene glycol and (ii) monoethers of polymers of ethylene and propylene glycols preferably constitute at least, with increasing preference in the order given, 12, 15, 17, 19.0, or 20.0% of the total composition. Independently of one another and of any other stated preferences: molecules selected from the group consisting of (i) homopolymers of ethylene glycol and (ii) monoethers of polymers of ethylene and propylene glycols preferably constitute not more than, with increasing preference in the order given, 50, 40, 35, 30, or 25% of the total composition; molecules selected from the group consisting of glycerin and propylene glycol preferably constitute not more than, with increasing preference in the order given, 40, 30, 25, 22, 19, 17, or 15 percent of the total composition; surfactants belonging to component (A) preferably constitute not more than, with increasing preference in the order given, 40, 30, 20, 15, 12, 10, 8, or 6% of the total composition; and component (A) in total constitutes not more than, with increasing preference in the order given, 90, 80, 70, 60, 50, 40, or 31% of the total composition, all of the preferences stated in this sentence being primarily for reasons of economy.

Ordinarily it is preferable if all of the surfactant in a composition to be used for forming a glossy and specularly reflective liquid film in a process according to the invention is part of component (A). In this instance, component (B) as described above is not needed and therefore preferably is not used. However, an antifoam agent that does not satisfy the conditions for belonging to component (A) may be needed in certain instances, as may other conventional surfactants, in order to achieve adequate and rapid wetting of the surface to be examined for defects. Highly fluorinated surfactants, for example, may be needed for plastics that have very low surface energies and are therefore difficult for most water-based compositions to wet. When fluorinated surfactants are needed for good wetting, they are preferably selected from the group consisting of fluorinated, preferably perfluorinated, alkyl substituted phosphonic, phosphinic, sulfonic, and sulfinic acids, more preferably phosphonic and phosphinic acids, and salts of these acids. When fluorinated surfactants are used, their total concentration in the liquid used to form a glossy and specularly reflective film in a process according to the invention preferably is at least, with increasing preference in the order given, 0.0020, 0.0040, 0.0060, 0.0080. 0.010, 0.012, 0.014, 0.016, or 0.018% and independently, primarily for reasons of economy, preferably is not more than, with increasing preference in the order given, 0.5, 0.3, 0.20, 0.10, 0.080, 0.060, 0.040, or 0.030%.

Care should be taken to avoid utilizing any surfactants that, in the concentrations of them used, are likely to penetrate into the interior of the substrate having a surface being tested and thereby physically weaken the substrate and/or weaken the adhesion of subsequently desired finishes to the surface. Preferably a composition according to the invention does not substantially swell or dissolve the organic solid to be tested. This property can conveniently be checked by placing a few drops of the composition on a sample of the surface to be tested, allowing the drops to remain in place on the surface for at least eight hours, and then rinsing off the composition and examining the surface for visible damage. Most preferably, no change in the surface to be tested is observable with the unaided eye after this test. In some cases, however, a faint haziness is observable in the tested surface after such an extended test, without any significant harm to the performance of the composition that causes the haze in practical use. Compositions that leave the surface visibly swollen, blistered, and/or tacky are preferably avoided.

Individual components can be tested in the same way as described above for the compositions, if the individual components are liquid, or in concentrated solutions if the components are solids at the intended temperature of use. Most surfactants tested in highly concentrated form have been found to promote swelling of some surfaces that might be tested in a process according to the invention, but alkyl polyglucosides are exceptional among strongly effective surfactants in lacking any such detrimental tendency. If a surfactant that is not part of component (A) as described above is needed or preferred in a composition for forming a substantially uniform and specularly reflective liquid film in a process according to the invention, therefore, this class of surfactants is preferred if the tendency for damage to the surface being tested needs to be minimized. However, as noted in the examples below, some surfactants, such as MONATERIC® Cy Na 50, that can safely be used at moderate concentrations cause damage when tested at a high concentration on at least some substrates that might be tested according to this invention.

Ordinarily water is a preferred component of a composition to be used for forming a glossy and specularly reflective liquid film in a process according to the invention, if for no other reason than reducing the cost of the composition. Thus, normally water preferably constitutes the balance of any amount of a composition to be used for forming a glossy and specularly reflective liquid film in a process according to the invention that is not specified to be some other substance. However, if a particularly long open time is needed for any reason, water may be omitted.

A composition to be used for forming a glossy and specularly reflective liquid film in a process according to the invention preferably has a pH value in a very mildly acidic to mildly alkaline range. More particularly, the pH preferably is at least, with increasing preference in the order given, 5.5, 6.0, 6.3, 6.6, 6.9, 7.1, 7.3, 7.6, 7.9, or 8.2 and, if the composition does not contain more than, with increasing preference in the order given, 5.0, 4.0, 3.0, 2.0, or 1.0% of glycol polymers and/or glycol polymer ethers, more preferably is at least, with increasing preference in the order given, 8.5, 8.8, 9.1, or 9.4; independently the pH preferably is not more than, with increasing preference in the order given, 11.0, 10.5, 10.2, 9.9, or 9.6, and, if the composition contains at least, with increasing preference in the order given, 6, 8, 10, 12, 14, or 16% of glycol polymers or glycol polymer ethers more preferably is not more than 9.3, or still more preferably not more than 9.0. In order to achieve a preferred pH, an alkalinizing pH adjusting component (D), in addition to any materials in components (A) through (C) as defined above, is generally needed. Aqueous ammonia or an amine is generally preferred for this purpose. If the pH is within its most preferred range, ammonia may normally be used without danger of a serious odor nuisance, but if more alkaline pH values are desired, a relatively non-volatile amine, preferably an amine with at least two and preferably three substituent moieties selected from the group consisting of hydroxymethyl, hydroxyethyl, and hydroxypropyl moieties, most preferably hydroxyethyl, are preferably used instead to avoid a malodorous composition. If an acidizing pH adjusting agent should be needed, numerous ones are known to those skilled in the art.

Normally, the presence of a preservative, component (E) as described above, in a composition to be used for forming a glossy and specularly reflective liquid film in a process according to the invention is highly preferred if the composition is to be stored in an open container during use as it usually is, because some commonly air-borne microorganisms with malodorous and/or otherwise disagreeable, e.g., surface-blemishing, metabolic products are readily attracted to and nourished by most of the constituents normally used for component (A). Any preservative with sufficient protective value against ambient micro-organisms may be used, provided that it does not adversely affect the wetting and/or specularly reflective properties of the liquid films formed in a process according to the invention. Preservatives containing isothiazolin-3-one moieties have been found particularly suitable, more particularly a mixture of the commercial products KATHON™ 886 MW and 893 MW preservatives from Rohm and Haas Co. of Philadelphia, Pa. KATHON™ 886 MW is reported by its supplier to contain 10–12% of 5-chloro-2-methyl-isothiazolin-3-one and 3–5% of 2-methyl-isothiazolin-3-one as its preservative active ingredients along with 14–18% of magnesium nitrate and 8–10% of magnesium chloride, all in water solution with water as the balance, and to be particularly effective against bacteria. KATHON™ 893 MW is reported by its supplier to contain 45–48% of 2-n-octyl-4-isothiazolin-3-one and 52–55% of propylene glycol. Accordingly, a composition to be used to form a glossy and specularly reflective liquid film in a process according to the invention preferably contains, independently for each material noted, at least, with increasing preference in the order given: 0.50, 0.75, 0.90, 1.00, 1.10, 1.20, 1.30, or 1.37 parts per million by weight of the total composition, hereinafter usually abbreviated as "ppm", of 5chloro-2-methyl-isothiazolin-3-one; 0.10, 0.20, 0.25, 0.30, 0.35, 0.40, 0.45, or 0.48 ppm of 2-methyl-isothiazolin-3-one; and 0.75, 1.00, 1.50, 2.00, 2.25, 2.45, 2.60, 2.75, or 2.90 ppm of 2-n-octyl-isothiazolin-3-one. Also, independently of other preferences and independently for each material noted, a composition to be used to form a glossy and specularly reflective liquid film jn a process according to the invention preferably contains not more than, with increasing preference in the order given: 10, 8, 6, 4.0, 3.0, 2.5, 2.0 or 1.5 ppm of 5-chloro-2-methyl-isothiazolin-3-one; 5, 3, 2.0, 1.5, 1.0, 0.8, 0.6, or 0.54 ppm of 2-methyl-isothiazolin-3-one; and 25, 15, 10, 8, 6, 5.0, 4.0, 3.7, 3.4, 3.2, or 3.0 ppm of 2-n-octyl-isothiazolin-3-one, all of the preferences stated in this sentence being primarily for reasons of economy.

The rheological properties of a composition to be used for forming a glossy and specularly reflective liquid film in a process according to the invention should be such as are needed to keep the film formed from draining from the surface during the open time needed for examination. Ordinarily, a satisfactory rheology can be achieved by proper selection of the materials constituting component (A) as described above when substantial amounts of polyethylene glycols are included among the materials constituting component (A). If needed, however, any other rheology modifying agent may be added to such a composition to be used for forming a glossy and specularly reflective liquid film in a process according to the invention without departing from the spirit of the invention, provided that the rheology modifying agent used does not adversely affect the specular reflection properties of the film formed. Acrylic acid polymers, natural gums, synthetic carbohydrate polymers, and other water soluble materials of this kind are normally preferred when needed. When most of component (A) is selected from glycerin and propylene glycol, as is preferred in one embodiment of the invention, a rheology modifying agent is preferably used as well. Particularly preferred is a polyacrylic acid thickening agent; such materials are readily available as aqueous solutions, dispersions, or both dispersions and solutions. When this type of thickening agent is used, its amount (as active polymer only) preferably is at least, with increasing preference in the order given, 0.004, 0.008, 0.016, 0.025, 0.030, 0.035, 0.040, 0.042, 0.044, or 0.046% of the total glossy and specularly reflective liquid film and independently preferably is not more than, with increasing preference in the order given, 0.30, 0.20, 0.10, 0.08, 0.060, 0.055, or 0.050% of the total glossy and specularly reflective liquid film.

Humectant component (G) is not normally needed or advantageous in a composition to be used for forming a glossy and specularly reflective liquid film in a process according to the invention, particularly if monomeric glycols as described above, most of which have humectant properties, are included as part of component (A). However, other humectants, such as calcium chloride, may also be added to the compositions if desired, particularly to achieve very long open times.

For a variety of reasons, almost always including at least the economic reason of avoiding an unnecessary component, it is preferred that compositions to be used for forming a glossy and specularly reflective liquid film in a process according to the invention should be substantially free from many ingredients, including some used in the prior art in compositions for detecting defects on metal surfaces. Specifically, independently for each preferably minimized component listed below, compositions to be used for forming a glossy and specularly reflective liquid film in a process according to the invention preferably contain, with increasing preference in the order given, no more than 1.0, 0.35, 0.10, 0.08, 0.04, 0.02, 0.01, 0.001, or 0.0002% of each of the following constituents, except for and to the extent that these constituents may be part of optional components explicitly described hereinabove: hexavalent chromium, cyanide ions, nitrite ions, coordinate complexing agents for divalent or higher valent metal cations; dispersed or emulsified chemical substances that are not soluble in water to an extent of at least, with increasing preference in the order given, 1.0, 2.0, 3.0, 4.0, 5.0, 6.0, 7.0, 8.0, or 9.0%; inorganic compounds of any of the halogen elements; and any compounds containing any one of the elements boron, beryllium, and all elements, except for alkali metals and halogens, that have an atomic number greater than or equal to 19.

Substrate surfaces that can be effectively inspected according to this invention include, but are not limited to, polyester sheet molding compound (hereinafter usually abbreviated as "SMC"), both primed and unprimed, the latter also often being called "raw"; poly{vinyl chloride} (hereinafter usually abbreviated as "PVC") homopolymers and copolymers; polyurethane and polyurea plastic surfaces such as those of objects made commercially by injection molding from these plastics; terpolymers of acrylonitrile, butadiene, and styrene (hereinafter usually abbreviated as "ABS"); poly{phenylene oxide} (hereinafter usually abbreviated as "PPO") and copolymers of "phenylene oxide" with other materials such as polyamides; polycarbonate (hereinafter usually abbreviated as "PCO") polymers and copolymers; and thermoplastic polyolefins (hereinafter usually abbreviated as "TPO"). The invention is especially advantageously applicable to primed and unprimed SMC and TPO surfaces, most preferably to TPO.

Application of the defect detecting composition to the surface to be tested may be made by any method that forms a satisfactory film. Spraying, roll coating, brushing, wiping with a saturated absorbent material such as cloth, and squeegeeing are all suitable methods. However, some methods, such as the use of perforated saturated cloth, introduce small air bubbles into the coating formed. These are generally undesirable, as they may interfere with observation of the consistent gloss that characterizes a defect free surface. However, highly satisfactory applications can be made with cloth or non-woven webs that do not have openings larger than, with increasing preference in the order given, 4.0, 3.0, 2.0, 1.0, 0.7, 0.4, or 0.2 millimeter in their largest dimension. If a highly absorbent web of this type is completely saturated, it is likely to apply a wastefully large amount of the defect detecting composition. Therefore, it is preferred that an absorbent material used as a carrier for the defect detecting composition in a process according to this invention, at the time when contacted with a substrate to be tested, contains a mass of the defect detecting composition that is not more than, with increasing preference in the order given, 5.0, 3.0, 2.0, 1.7, 1.5, 1.35, 1.25, 1.15, 1.10, 1.05, or 1.00 times the mass of the absorbent material itself.

Practice of this invention may be further appreciated from consideration of the working and comparison examples described below.

COMPARISON EXAMPLE GROUP A

Kerosine, a hydrocarbon solvent with an initial boiling point of about 175° C. that has been used on metal surfaces for purposes analogous to those of this invention on non-metal surfaces, does not spread satisfactorily over TPO and SMC plastics to form a suitably glossy and speculary reflective film, and/or does not stay in place as much as five minutes when a sample coated with it is suspended with the coated surface vertical.

Similarly, a mixture of naphtha and mineral spirits has been used for metal surfaces, but it is entirely unsatisfactory for many plastic surfaces, because it can be absorbed by the plastic surfaces and be very difficult to remove from them, as is necessary for satisfactory further processing of the plastic objects having surfaces contaminated with these volatile compounds. In addition, this material has a flash point below 38° C. and therefore is a substantial fire hazard.

GROUP 1—WITH COMPOSITIONS GENERALLY INCLUDING GLYCOL POLYMERS AND/OR GLYCOL POLYMER ETHERS

Compositions for this group are given in Table 1 below. The performance of the compositions shown in Table 1 on various plastic substrates, in most instances including TPO, which is generally considered one of the most difficult of the engineering plastics to wet consistently, is as follows:

Composition 1.1 wets some plastics well and others such as TPO, on which it is susceptible to Swiss-cheese-dewetting, less well. It becomes non-glossy within 15 rain after application on any substrate tried. It washes off easily with water, even after losing its gloss, and has no visible effect on the washed plastic surface.

Composition 1.2, which is considerably more concentrated in glycol polymers and in some of the surfactants but has the same ingredients as Composition 1, behaves essentially as does Composition 1.1.

Composition 1.3 is one of the best and most economical of this group, with an open time of at least 3–4 minutes on any substrate tried, including TPO and bare and primed SMC, on the latter of which it dries without ever collecting into drops.

Composition 1.4 has the same ingredients as Composition 1.3, except that the glycol polymers are omitted. It provides excellent initial properties but has no more than 2 minutes of open time, demonstrating an advantage of the glycol polymers.

Composition 1.5 has the same ingredients as Composition 1.3, but with considerably higher concentrations of the glycol polymers. It is considerably more viscous than and forms a thicker coating than Composition 1.3, but the open time is not significantly improved over Composition 1.3, demonstrating the lack of additional benefit from greater concentrations of glycol polymers.

Compositions 1.6 and 1.7 are the most troublefree of this group but are more expensive than Composition 1.3, which often gives quite adequate results. Compositions 1.6 and 1.7 both achieve very high quality coatings which do not show Swiss-cheese-dewetting

TABLE 1

LIQUID COMPOSITIONS FOR POSSIBLE USE IN DETECTING DEFECTS IN PLASTIC SURFACES

| Ingredient and Concentration Unit | Concentration of Ingredient in Composition Number: | | | | | | | |
|---|---|---|---|---|---|---|---|---|
| | 1.1 | 1.2 | 1.3 | 1.4 | 1.5 | 1.6 | 1.7 | 1.8 |
| Polyethylene glycol, 1000 Mo Wg, % | 5.7 | 12 | 9.7 | | 25 | | | 10 |
| Polyethylene glycol, 400 Mo Wg, % | 1.1 | 12 | 9.7 | | 25 | 17 | | 10 |
| 96% Glycerin, % | 15 | | | | | | | |
| Dipropylene glycol, mono-n-propyl ether, % | | | | | | | 10 | |

TABLE 1-continued

LIQUID COMPOSITIONS FOR POSSIBLE USE IN DETECTING DEFECTS IN PLASTIC SURFACES

| Ingredient and Concentration Unit | Concentration of Ingredient in Composition Number: | | | | | | | |
|---|---|---|---|---|---|---|---|---|
| | 1.1 | 1.2 | 1.3 | 1.4 | 1.5 | 1.6 | 1.7 | 1.8 |
| MONATERIC ™ Cy Na 50 surfactant sol., % | | 3.1 | | | | 2.5 | | 2.0 |
| PLURONIC ™ L-64 surfactant, % | 3.5 | 2.6 | 4.0 | 7.0 | 4.0 | | | 1.7 |
| ANTAROX ™ LF-344 surfactant, % | 0.5 | 0.4 | | | | | | 0.3 |
| ANTAROX ™ LF-224 surfactant, % | | | 1.7 | 1.7 | 1.7 | | | |
| TRITON ™ N-57 surfactant, % | | | 0.3 | 0.3 | 0.3 | | | |
| PLURAFAC ™ RA-40 surfactant, % | | | | | | | 30 | |
| PLURAFAC ™ RA-30 surfactant, % | | | | | | 2.2 | | |
| PLURAFAC ™ RA-20 surfactant, % | | | | | | 0.9 | | |
| TRITON ™ DF-12 surfactant, % | | | | | | 0.4 | | |
| Dee Fo ™ 97-3 antifoam agent, % | | | | | | | 0.04 | |
| FLUOWET ™ PL80 surfactant, % | | | | | | 0.09 | | |
| 28% Ammonia in water, ppt | 0.5 | 0.5 | 0.5 | 0.5 | 0.5 | | | 0.5 |
| Triethanol amine, % | | | | | | 0.7 | 1.1 | |
| KATHON ™ 886 MW, ppm | 13 | 13 | 13 | 13 | 13 | 13 | 13 | 13 |
| KATHON ™ 893 MW, ppm | 6.4 | 6.4 | 6.4 | 6.4 | 6.4 | 6.4 | 6.4 | 6.4 |
| ACUSOL ™ 810 thickening agent | | | | | | 0.6 | | |

Abbreviations and Other Notes for Table 1
"Mo Wg" means "weight average molecular weight"; "sol." means "solution in water"; "ppt" means "parts per thousand". A blank space in a cell of the upper part of this and any subsequent table indicates that none of the material named in the row containing the cell was added to the composition.
Water constituted the unspecified balance of the compositions shown in this table.
PLURONIC ™ L-64 and PLURAFAC ™ RA-40, -30, and -20 surfactants were obtained commercially from BASF Corp. and were reported by their supplier to be block copolymers of propylene and ethylene oxide for the first listed and modified oxyethylated straight chain alcohols for the remainder. ANTAROX ™ LF-344 and LF 224 were obtained commercially from Rhone-Poulenc and were reported by their supplier to be modified linear aliphatic polyether and alkoxylated alcohol respectively.
TRITON ™ N-57 and DF-12 surfactants were obtained commercially from Union Carbide and are reported by their supplier to be nonylphenoxypolyethoxyethanol and modified polyethoxylated straight chain alcohol respectively. FLUOWET ™ PL80 surfactant was obtained commercially from Minnesota Mining and Manufacturing Co. and was reported by its supplier to be perfluorinated alkyl phosphonic and phosphinic acids.
ACUSOL ™ 810 thickening agent was obtained commercially from Rohm & Haas and was reported by its supplier to be a 15–19% solution in water of polyacrylic acid. Dee Fo ™ 97-3 was obtained commercially from Ultra Additives, Inc., Paterson, New Jersey (no chemical information about it was given, except that it contained 4% petroleum solvent.).

on any of the substrates TPO and bare and primed SMC, have at least 5 minutes of open time, remain glossy even after drying, and can readily be removed by water rinsing.

Composition 1.8 is susceptible to such severe Swiss-cheese-dewetting that it has no more than 90 seconds of effective open time.

GROUP 2—WITH COMPOSITIONS INCLUDING MONOMERIC GLYCOLS AS PREDOMINANT CONSTITUENTS OF COMPONENT (A)

Compositions for this group are shown in Table 2 below.

Characteristics in use of the compositions shown in Table 2 are as follows:

Compositions 2.1 and 2.2 flow out well on both SMC and TPO substrates, producing a glossy film that persists for at least several hours. On SMC, a hydrophilic slick area is produced after the initially formed film, having been in place for several hours, is rinsed away with water. No such hydrophilic slick forms on TPO substrate.

Both of Compositions 2.3 and 2.4 flow out readily onto both SMC and TPO and have open times of at least 30

TABLE 2

MORE LIQUID COMPOSITIONS FOR POSSIBLE USE IN DETECTING DEFECTS IN PLASTIC SURFACES

| Ingredient | Parts by Weight of Ingredient in Composition Number: | | | | | | | |
|---|---|---|---|---|---|---|---|---|
| | 2.1 | 2.2 | 2.3 | 2.4 | 2.5 | 2.6 | 2.7 | 2.8 |
| Deionized Water | 120 | 120 | 138 | 126 | 135 | 135 | 135 | 156 |
| AMPHOTERGE ™ KJ-2 surfactant | 7.5 | 7.5 | 1.5 | 1.5 | 4.5 | 4.5 | 4.5 | 4.5 |
| 96% Glycerin | 21.5 | 21.5 | 21.5 | | 21.5 | 21.5 | 21.5 | |
| Ethylene glycol | | | | 21.5 | | | | |
| FLUOWET ™ PL80 surfactant, % | 0.10 | 0.01 | 0.03 | 0.03 | 0.03 | 0.03 | | 0.03 |
| ACUSOL ™ 810 thickening agent | 0.9 | 0.9 | 0.9 | 0.9 | 0.45 | | | |
| Other Characteristics of Composition: | 2.1 | 2.2 | 2.3 | 2.4 | 2.5 | 2.6 | 2.7 | 2.8 |
| Concentration of KATHON ™ 886 MW, ppm: | 13 | 13 | 13 | 13 | 13 | 13 | 13 | 13 |
| Concentration of KATHON ™ 893 MW, ppm: | 6.4 | 6.4 | 6.4 | 6.4 | 6.4 | 6.4 | 6.4 | 6.4 |
| pH of the Composition: | 9.4 | 9.4 | 7.9 | n.m. | 9.4 | n.m. | n.m. | n.m. |

Abbreviation for Table 2
"n.m." means "not measured".

minutes. However, after storage of the coated part for 16 hours, with exposure to the ambient atmosphere, Composition 2.4 has a dry look, while Composition 2.3 still looks glossy. Most residues from both Compositions are easily removed from the substrates after this 16 hour period of exposure, but, as with Compositions 2.1 and 2.2, a hydrophilic slick remains on the SMC substrate only after rinsing, while the rinsed substrates are still wet. If the rinsed substrates are dried in an oven, no visible evidence of the hydrophilic slick remains, but the substrates do not wet easily with solvent-based paint in areas exposed to composition 2.4; little or no such lyophobicity is observed for the substrates exposed to Composition 2.3, indicating that glycerin causes less difficulty in this respect than does ethylene glycol.

Composition 2.5 on a TPO substrate, whether applied with a cotton swab or by flowing on, forms a suitable glossy film without any visually perceptible dewetting and with an open time of at least an hour. Composition 2.8 acts in the same way as 2.5, except that the film from Composition 2.8 is dull rather than glossy after a few minutes exposure to the ambient atmosphere. Composition 2.7 dewets rapidly by "rolling up" of liquid from the edges of the coated area toward its center, after application by either method. Composition 2.6 is susceptible to rolling up when applied with a cotton swab but not when flowed on, a method that forms a thicker coating layer. After washing and drying, all of the surfaces treated with one of these four Compositions were free from visible residue and otherwise undamaged by the Compositions.

GROUP 3—TESTING COMPONENTS FOR ADVERSE EFFECTS ON SUBSTRATES

In a first subgroup, various candidate components were tested for possible damage to substrates. A few drops of each component were placed on the surface of test substrates as described further below and allowed to stand for 8 hours in air at 49° C. and 25% RH; then the residue of the liquid was rinsed away with 60 seconds of water spraying. The substrates tested and their identifying numbers are:

1. U04AD045 gray primer from BASF Corporation
2. Premix gray SMC primer from Siebert-Oxidermo Corporation
3. XENOY™ polycarbonate/polyester blend plastic from General Electric of Schenectady, N.Y.
4. Red Spot Paint Company type 206LE 2K Polyurethane Topcoat, white
5. "80° Gloss" RIM primer from PPG Corporation of Pittsburgh, Penn.

The components tested and their identifying abbreviations (in parentheses) are: APG® 225 (Apg2) and APG® 325 (Apg3) from Henkel Corp. of Plymouth Meeting, Pennsylvania; Triton® DF-16 (DF-16); MAKON® NF-12 (NF-12); MONATERIC® Cy Na 50 (MON) and PLURONIC® L63 (PLU). The results are shown in Table 3. Only glycerin and the APG® surfactants were generally free from any evidence of damage when applied in full strength as in this test, but many of the other components listed can be used in the amounts preferred for compositions to be used to form a substantially uniform and specularly reflective liquid film in a process according to this invention, without causing any unacceptable damage to the surfaces tested.

In a second subgroup, the following components and component mixtures were tested in exposure for about 16 hours on raw SMC: (1) glycerin alone, (2) AMPHOTERGE™ KJ-2 surfactant alone, (3) ACCUSOL™ 810 rheology modifying agent alone, (4) FLUOWET™ PL-80 surfactant alone, (5) glycerin and the rheology modifying agent mixture, (6) glycerin and KJ-2 surfactant mixture, and (7) glycerin and PL-80 surfactant mixture. After rinsing with warm tap water, (1), (2), and (6) had no visible effect on the substrate; (3) and (5) hydrophilicized the SMC surface arid (5) slightly darkened it; and (4) and (7) both hydrophilicized the SMC surface and changed its color, (7) even leaving a whitish residue on the surface.

TABLE 3

RESULTS OF TESTS OF SURFACTANTS FOR DAMAGE TO SUBSTRATES

| Component | Evidence of Damage on Substrate No.: | | | | |
|---|---|---|---|---|---|
| | 1 | 2 | 3 | 4 | 5 |
| Apg2 | trace | none | none | none | none |
| Apg3 | none | none | none | none | none |
| DF 16 | slick | shiny raised area | haze damage | whitish raised bump | bump |
| MON | trace | trace | haze damage | slight raised area | raised area |
| NF 12 | glossy raised slick | glossy, slightly raised | haze damage | raised area | raised area |
| PLU | glossy raised slick | glossy, slightly raised | raised area | raised area | raised area |

The invention claimed is:

1. A process for determining whether a non-metallic surface having a matte finish includes any geometrical irregularities that are not readily visually detectable while the surface remains unreflective, said process comprising steps of:

(I) covering all parts of the non-metallic surface on which a determination of presence or absence of said geometrical irregularities is to be made with a glossy and specularly reflective liquid film that comprises:

(A) a concentration of a dissolved component consisting of one or more organic substances each molecule of which contains at least one continuously chemically bonded chain or ring of atoms in which there are at least two carbon atoms and at least two heteroatoms selected from the group consisting of oxygen, nitrogen, sulfur, and phosphorus atoms, said carbon atoms and said heteroatoms being arranged in such an order along said continuously chemically bonded chain or ring that (i) each heteroatom is bonded to at least one carbon atom and (ii) the chain does not include more than three consecutive continuously chemically bonded carbon atoms; and (II) visually examining reflectivity of light from all parts of the glossy and specularly reflective liquid film formed over the non-metallic surface in step (I), and determining whether the reflectivity of light is visually uniform over all parts of the glossy and specularly reflective liquid film.

2. A process according to claim 1, wherein said glossy and specularly reflective film, when it is first applied as a covering over the non-metallic surface, comprises water and at least about 5.0% of component (A) as defined in claim 1 and has a pH value within the range from about 5.5 to about 11.0.

3. A process according to claim 2, wherein said glossy and specularly reflective film, when it is first applied as a covering over the non-metallic surface, has a pH value within the range from about 6.3 to about 10.2 and comprises at least about 0.50% of surfactants belonging to component (A) and at least about 4.5% of molecules selected from the group consisting of (i) homopolymers of ethylene glycol; (ii) monoethers of homopolymers of ethylene glycol, monoethers of homopolymers of propylene glycol, and monoethers of copolymers of ethylene and propylene glycols; and (iii) glycerin and propylene glycol.

4. A process according to claim 3, wherein said glossy and specularly reflective film, when it is first applied as a covering over the non-metallic surface, has a pH value within the range from about 7.6 to about 9.9 and comprises at least about 0.70% of surfactant molecules each of which contains an alkyl imidazoline moiety and at least about 6.0% of a total of glycerin and propylene glycol.

5. A process according to claim 4, wherein said glossy and specularly reflective film, when it is first applied as a covering over the non-metallic surface, has a pH value within the range from about 8.5 to about 9.9 and comprises: (i) from about 1.0 to about 6% of surfactant molecules each of which contains an alkyl imidazoline moiety that comprises, chemically bonded to a nitrogen atom in the imidazoline moiety, at least one substituent moiety selected from the group consisting of hydroxyalkyl moieties, carboxyalkyl moieties, and carbonate moieties; (ii) from about 12.0 to about 31% of a total of glycerin and propylene glycol; (iii) at least 0.012% of surfactant selected from the group consisting of fluorinated esters of phosphoric and phosphinic acids; (iv) from about 0.035 to about 0.060% of acrylic acid thickening agent; (v) a preservative-effective amount of a preservative component selected from the group consisting of molecules each of which includes at least one isothiazolin-3-one moiety; and not more than about 1.0% of a total of glycol polymers and glycol polymer ethers.

6. A process according to claim 5, wherein said non-metallic surface is a surface of thermoplastic polyolefin.

7. A process according to claim 1, wherein said non-metallic surface is a surface of thermoplastic polyolefin.

8. A process according to claim 3, wherein said glossy and specularly reflective film, when it is first applied as a covering over the non-metallic surface, has a pH value within the range from about 7.6 to about 9.9 and comprises: (i) at least about 0.70% of surfactant molecules each of which contains an alkyl imidazoline moiety; (ii) at least about 12% of molecules selected from the group consisting of (ii.1) homopolymers of ethylene glycol and (ii.2) monoethers of polymers of (ii.2.1) ethylene glycol, (ii.2.2) propylene glycol, and (ii.2.3) both ethylene and propylene glycols; and (iii) not more than 6.0% of a total of glycerin and propylene glycol.

9. A process according to claim 8, wherein said glossy and specularly reflective film, when it is first applied as a covering over the non-metallic surface, has a pH value within the range from about 8.8 to about 9.3 and comprises: (i) from about 1.0 to about 6% of surfactant molecules each of which contains an alkyl imidazoline moiety that comprises, chemically bonded to a nitrogen atom in the imidazoline moiety, at least one substituent moiety selected from the group consisting of hydroxyalkyl moieties, carboxyalkyl moieties, and carbonate moieties; (ii) from about 17 to about 25% of a total of molecules selected from the group consisting of (ii.1) homopolymers of ethylene glycol and (ii.2) monoethers of polymers of (ii.2.1) ethylene glycol, (ii.2.2) propylene glycol, and (ii.2.3) both ethylene and propylene glycols; (iii) at least 0.012% of surfactant selected from the group consisting of fluorinated esters of phosphoric and phosphinic acids; (iv) from about 0.035 to about 0.060% of acrylic acid thickening agent; (v) a preservative-effective amount of a preservative component selected from the group consisting of molecules each of which includes at least one isothiazolin-3-one moiety; and (vi) not more than 1.0% of a total of glycerin and propylene glycol.

10. A process according to claim 9, wherein said non-metallic surface is a surface of thermoplastic polyolefin.

11. A process according to claim 9, wherein said glossy and specularly reflective film, when it is first applied as a covering over the non-metallic surface, has a pH value within the range from about 7.6 to about 9.9 and has been made by mixing into the liquid constituting said glossy and specularly reflective film: (i) at least about 0.70% of surfactant molecules each of which contains an alkyl imidazoline moiety; (ii) at least about 12% of molecules selected from the group consisting of (ii.1) homopolymers of ethylene glycol and (ii.2) monoethers of polymers of (ii.2.1) ethylene glycol, (ii.2.2) propylene glycol, and (ii.2.3) both ethylene and propylene glycols; and (iii) not more than 6.0% of a total of glycerin and propylene glycol.

12. A process according to claim 11, wherein said glossy and specularly reflective film has a pH value within the range from about 8.8 to about 9.3 and has been made by mixing into the liquid constituting said glossy and specularly reflective film: (i) from about 1.0 to about 6% of surfactant molecules each of which contains an alkyl imidazoline moiety that comprises, chemically bonded to a nitrogen atom in the imidazoline moiety, at least one substituent moiety selected from the group consisting of hydroxyalkyl moieties, carboxyalkyl moieties, and carbonate moieties; (ii) from about 17 to about 25% of a total of molecules selected from the group consisting of (ii.1) homopolymers of ethylene glycol and (ii.2) monoethers of polymers of (ii.2.1) ethylene glycol, (ii.2.2) propylene glycol, and (ii.2.3) both ethylene and propylene glycols; (iii) at least 0.012% of surfactant selected from the group consisting of fluorinated esters of phosphoric and phosphinic acids; (iv) from about 0.035 to about 0.060% of acrylic acid thickening agent; (v) a preservative-effective amount of a preservative component selected from the group consisting of molecules each of which includes at least one isothiazolin-3-one moiety; and, (vi) not more than 1.0% of a total of glycerin and propylene glycol.

13. A process according to claim 12, wherein said non-metallic surface is a surface of thermoplastic polyolefin.

14. A process for determining whether a non-metallic surface having a matte finish includes any geometrical irregularities that are not readily visually detectable while the surface remains unreflective, said process comprising steps of:

(I) covering all parts of the non-metallic surface on which a determination of presence or absence of said geometrical irregularities is to be made with a glossy and specularly reflective liquid film that has been made by mixing with one another:

(A) a concentration of a water soluble component consisting of one or more organic substances each molecule of which contains at least one continuously chemically bonded chain or ring of atoms in which there are at least two carbon atoms and at least two heteroatoms selected from the group consisting of oxygen, nitrogen, sulfur, and phosphorus atoms, said carbon atoms and said heteroatoms being arranged in such an order along said continuously chemically bonded chain or ring that (i) each heteroatom is bonded to at least one carbon atom and (ii) the chain does not include more than three consecutive continuously chemically bonded carbon atoms; and (B) water; and (II) visually examining reflectivity of light from all parts of the glossy and specularly reflective liquid film formed over the non-metallic surface in step (I), and determining whether the reflectivity of light is visually uniform over all parts of the glossy and specularly reflective liquid film.

15. A process according to claim 14, wherein said glossy and specularly reflective film, when it is first applied as a covering over the non-metallic surface, has a pH value within the range from about 5.5 to about 11.0 and has been made by mixing water and an amount of component (A) as defined in claim 1 that constitutes at least about 5.0% of the total glossy and specularly reflective film.

16. A process according to claim 15, wherein said glossy and specularly reflective film, when it is first applied as a covering over the non-metallic surface, has a pH value within the range from about 6.3 to about 10.2 and has been made by mixing into the liquid constituting said glossy and specularly reflective film at least about 0.50% of surfactants belonging to component (A) and at least about 4.5% of molecules selected from the group consisting of (i) homopolymers of ethylene glycol; (ii) monoethers of homopolymers of ethylene glycol, monoethers of homopolymers of propylene glycol, and monoethers of copolymers of ethylene and propylene glycols; and (iii) glycerin and propylene glycol.

17. A process according to claim 16, wherein said glossy and specularly reflective film, when it is first applied as a covering over the non-metallic surface, has a pH value within the range from about 7.6 to about 9.9 and has been made by mixing into the liquid constituting said glossy and specularly reflective film at least about 0.70% of surfactant molecules each of which contains an alkyl imidazoline moiety and at least about 6.0% of a total of glycerin and propylene glycol.

18. A process according to claim 17, wherein said glossy and specularly reflective film, when it is first applied as a covering over the non-metallic surface, has a pH value within the range from about 8.5 to about 9.9 and has been made by mixing into the liquid constituting said glossy and specularly reflective film: (i) from about 1.0 to about 6% of surfactant molecules each of which contains an alkyl imidazoline moiety that comprises, chemically bonded to a nitrogen atom in the imidazoline moiety, at least one substituent moiety selected from the group consisting of hydroxyalkyl moieties, carboxyalkyl moieties, and carbonate moieties; (ii) from about 12.0 to about 31% of a total of glycerin and propylene glycol; (iii) at least 0.012% of surfactant selected from the group consisting of fluorinated esters of phosphoric and phosphinic acids; (iv) from about 0.035 to about 0.060% of acrylic acid thickening agent; (v) a preservative-effective amount of a preservative component selected from the group consisting of molecules each of which includes at least one isothiazolin-3-one moiety; and not more than about 1.0% of a total of glycol polymers and glycol polymer ethers.

19. A process according to claim 18, wherein said non-metallic surface is a surface of thermoplastic polyolefin.

20. A process according to claim 14, wherein said non-metallic surface is a surface of thermoplastic polyolefin.

* * * * *